US008786691B2

(12) United States Patent
Koide (10) Patent No.: US 8,786,691 B2
(45) Date of Patent: Jul. 22, 2014

(54) BIOMEDICAL RECEIVER AND SENSOR SYSTEM FOR PHYSIOLOGICAL MONITORING OF PATIENTS (75) Inventor: Naoto Koide, Hachioji (JP)

(73) Assignee: Olympus Medical Systems Corp., Tokyo (JP)

(*) Notice: Subject to any disclaimer, the term of this patent is extended or adjusted under 35 U.S.C. 154(b) by 96 days.

(21) Appl. No.: 13/089,618

(22) Filed: Apr. 19, 2011

(65) Prior Publication Data

US 2011/0285835 A1 Nov. 24, 2011

Related U.S. Application Data (63) Continuation of application No. PCT/JP2010/061409, filed on Jul. 5, 2010.

(30) Foreign Application Priority Data

Aug. 28, 2009 (JP) ................................. 2009-198606

(51) Int. Cl.
*A61B 1/04* (2006.01)
*A61B 5/07* (2006.01)
*A61B 1/00* (2006.01)

(52) U.S. Cl.
CPC ............. *A61B 1/041* (2013.01); *A61B 5/073* (2013.01); *A61B 1/00036* (2013.01); *A61B 1/00016* (2013.01)
USPC ........................................................ 348/76

(58) Field of Classification Search
USPC .......................................................... 348/76
See application file for complete search history.

(56) References Cited

U.S. PATENT DOCUMENTS 4,183,053 A * 1/1980 Tomii et al. ................... 348/812
4,602,281 A * 7/1986 Nagasaki et al. ............... 348/69
4,736,097 A * 4/1988 Philipp ........................... 250/221
(Continued)

FOREIGN PATENT DOCUMENTS

EP  2 011 430 A1  1/2009
JP  2003-144417   5/2003
(Continued)

OTHER PUBLICATIONS

International Search Report dated Aug. 10, 2010.
(Continued)

*Primary Examiner* — Dave Czekaj
*Assistant Examiner* — Kehinde O Abimbola
(74) *Attorney, Agent, or Firm* — Scully, Scott, Murphy & Presser, P.C.

(57) ABSTRACT

An object is to provide a receiver system that allows a plurality of antennas to be easily attached onto a body surface without losing receiving functions of the antennas while improving freedom for a living body. A receiver system transmits in-vivo information including in-vivo images received from a capsule endoscope being the interior of a subject to an exterior receiving device via a plurality of wireless relay devices. Each of the wireless relay devices includes a receiving unit that receives the in-vivo information from the capsule endoscope at a first frequency, a transmitting unit that transmits the in-vivo information at a second frequency, a receiving unit that receives a control signal transmitted by the receiving device at the second frequency, and a control unit that controls transmissions and receptions performed by the receiving unit and the transmitting unit based on the control signal.

14 Claims, 10 Drawing Sheets

(56) References Cited

U.S. PATENT DOCUMENTS

| | | | |
|---|---|---|---|
| 4,750,032 A * | 6/1988 | Nakayama | 348/225.1 |
| 4,875,107 A * | 10/1989 | Heidt et al. | 386/224 |
| 5,237,407 A * | 8/1993 | Crezee et al. | 348/89 |
| 5,920,360 A * | 7/1999 | Coleman, Jr. | 348/700 |
| 6,552,642 B1 * | 4/2003 | Toi et al. | 336/192 |
| 7,191,013 B1 * | 3/2007 | Miranda et al. | 607/60 |
| 7,196,608 B2 * | 3/2007 | Hirai et al. | 336/200 |
| 7,419,468 B2 * | 9/2008 | Shimizu et al. | 600/117 |
| 7,596,359 B2 * | 9/2009 | Kimoto et al. | 455/137 |
| 7,676,258 B2 * | 3/2010 | Eastman | 600/476 |
| 7,724,928 B2 * | 5/2010 | Glukhovsky et al. | 382/128 |
| 7,865,229 B2 * | 1/2011 | Horn | 600/424 |
| 7,978,932 B2 * | 7/2011 | Vercauteren et al. | 382/284 |
| 8,038,599 B2 * | 10/2011 | Kimoto et al. | 600/118 |
| 8,038,601 B2 * | 10/2011 | Shimizu et al. | 600/118 |
| 8,177,715 B2 * | 5/2012 | Chiba et al. | 600/301 |
| 8,204,441 B2 * | 6/2012 | Koide | 455/41.2 |
| 2002/0159948 A1 * | 10/2002 | Adair et al. | 424/1.49 |
| 2002/0173718 A1 * | 11/2002 | Frisch et al. | 600/424 |
| 2003/0001956 A1 * | 1/2003 | Harshbarger et al. | 348/189 |
| 2004/0193020 A1 | 9/2004 | Chiba et al. | |
| 2004/0215083 A1 * | 10/2004 | Shimizu et al. | 600/473 |
| 2004/0225190 A1 | 11/2004 | Kimoto et al. | |
| 2005/0143647 A1 * | 6/2005 | Minai et al. | 600/410 |
| 2005/0194012 A1 | 9/2005 | Ito et al. | |
| 2006/0106304 A1 * | 5/2006 | Eastman | 600/431 |
| 2006/0120484 A1 | 6/2006 | Matsumoto et al. | |
| 2006/0264734 A1 * | 11/2006 | Kimoto et al. | 600/407 |
| 2007/0010711 A1 * | 1/2007 | Hasegawa | 600/168 |
| 2007/0185382 A1 * | 8/2007 | Shimizu et al. | 600/118 |
| 2007/0217686 A1 * | 9/2007 | Yamamoto | 382/218 |
| 2008/0002734 A1 * | 1/2008 | Zheng et al. | 370/445 |
| 2008/0033242 A1 | 2/2008 | Tamura | |
| 2008/0143822 A1 * | 6/2008 | Wang et al. | 348/36 |
| 2008/0186380 A1 * | 8/2008 | Zhang et al. | 348/143 |
| 2008/0227394 A1 * | 9/2008 | Homan et al. | 455/41.3 |
| 2009/0003732 A1 | 1/2009 | Oda | |
| 2009/0054731 A1 | 2/2009 | Shigemori | |
| 2009/0072171 A1 * | 3/2009 | So et al. | 250/584 |
| 2009/0137883 A1 * | 5/2009 | Chiba et al. | 600/302 |
| 2009/0163771 A1 * | 6/2009 | Kimoto et al. | 600/118 |
| 2009/0163772 A1 * | 6/2009 | Koide et al. | 600/118 |
| 2009/0203964 A1 | 8/2009 | Shimizu et al. | |
| 2009/0318760 A1 | 12/2009 | Pascal et al. | |
| 2009/0318766 A1 | 12/2009 | Rabinovotz et al. | |
| 2010/0045778 A1 * | 2/2010 | Yelin | 348/45 |
| 2010/0115469 A1 | 5/2010 | Shigemori | |
| 2010/0123835 A1 * | 5/2010 | Ichikawa | 348/734 |
| 2010/0157041 A1 * | 6/2010 | Klaiman et al. | 348/77 |
| 2010/0286674 A1 * | 11/2010 | Ben-Yakar et al. | 606/10 |
| 2011/0063127 A1 * | 3/2011 | Matsumoto et al. | 340/870.03 |
| 2011/0261262 A1 * | 10/2011 | Vercauteren et al. | 348/607 |
| 2011/0285835 A1 * | 11/2011 | Koide | 348/76 |
| 2011/0286536 A1 * | 11/2011 | Koide | 375/259 |
| 2012/0259385 A1 * | 10/2012 | McElveen, Jr. | 607/57 |
| 2012/0262560 A1 * | 10/2012 | Nisani et al. | 348/68 |
| 2012/0287244 A1 * | 11/2012 | Bennett et al. | 348/46 |

FOREIGN PATENT DOCUMENTS

| | | |
|---|---|---|
| JP | 2005-245938 | 9/2005 |
| JP | 2006-181359 | 7/2006 |
| JP | 2007-117285 | 5/2007 |
| JP | 2007-143820 | 6/2007 |
| JP | 2007-215957 | 8/2007 |
| JP | 2007-289528 | 11/2007 |
| JP | 2008-053894 | 3/2008 |
| JP | 2008-099734 | 5/2008 |
| JP | 2008-119057 | 5/2008 |
| JP | 2008-278355 | 11/2008 |
| JP | 2008-295490 | 12/2008 |
| JP | 2009-005866 | 1/2009 |
| JP | 2009-118883 | 6/2009 |
| JP | 2009-136415 | 6/2009 |
| JP | 2009-521978 | 6/2009 |
| JP | 2009-165706 | 7/2009 |
| JP | 2009-189475 | 8/2009 |
| WO | 2004/096028 A1 | 11/2004 |
| WO | 2007/113839 A2 | 10/2007 |
| WO | WO 2008/120128 A2 | 10/2008 |

OTHER PUBLICATIONS

Extended European Search Report dated Mar. 28, 2013 issued in EP 10811611.2.

* cited by examiner

BIOMEDICAL RECEIVER AND SENSOR SYSTEM FOR PHYSIOLOGICAL MONITORING OF PATIENTS

CROSS-REFERENCE TO RELATED APPLICATIONS

This application is a continuation of PCT international application Ser. No. PCT/JP2010/061409 filed on Jul. 5, 2010 which designates the United States, incorporated herein by reference, and which claims the benefit of priority from Japanese Patent Application No. 2009-198606, filed on Aug. 28, 2009, incorporated herein by reference.

BACKGROUND OF THE INVENTION

1. Field of the Invention

The present invention relates to a receiver system for transmitting in-vivo information including in-vivo images transmitted from a capsule endoscope being located in a subject to a receiving device being outside of the living body via a plurality of wireless relay devices that are disposed on the outer surface of the living body.

2. Description of the Related Art

In the field of endoscopes, a capsule endoscope, which has a capsule-shaped casing enclosing therein an imaging function and a wireless communication function, has been introduced in recent years as an in-vivo image obtaining device for obtaining in-vivo images. A capsule endoscope is carried through internal organs such as stomach or small intestine by peristaltic motions and the like while capturing a series of in-vivo images of a subject, e.g., a patient, at a predetermined interval during a period from when the capsule endoscope is orally swallowed by the subject for the purpose of observation (examination) to when the endoscope is naturally excreted from the subject. The capsule endoscope sequentially transmits the in-vivo images thus captured (obtained) wirelessly.

A receiving device carried by the subject sequentially receives the in-vivo images transmitted by the capsule endoscope wirelessly. The receiving device includes a recording medium mounted on the receiving device in a removable manner, and stores a set of in-vivo images received from the capsule endoscope being located in the subject in the recording medium. The recording medium with the set of in-vivo images of the subject recorded therein is then removed from the receiving device, and mounted onto an image display device. The image display device obtains the set of in-vivo images of the subject via the storage medium, and displays the set of in-vivo images of the subject onto a display. Using an in-vivo image acquiring system including the capsule endoscope, the receiving device, and the image display device, a user such as a doctor or a nurse causes the set of in-vivo images captured by the capsule endoscope to be displayed onto the image display device to observe (examine) the interior of the internal organs of the subject through the set of in-vivo images.

Patent Document 1: Japanese Patent Application Laid-open No. 2003-144417
Patent Document 2: Japanese Patent Application Laid-open No. 2008-53894
Patent Document 3: Japanese Patent Application Laid-open No. 2007-215957

SUMMARY OF THE INVENTION

A receiver system according to an aspect of the present invention includes a capsule endoscope that is introduced into a subject and transmits in-vivo information including an in-vivo image; a plurality of wireless relay devices that are disposed on an outer surface of the subject and relay the in-vivo information transmitted by the capsule endoscope; and a receiving device that is located outside of the subject and receives the in-vivo information relayed by the wireless relay devices. Each of the wireless relay devices includes an interior side receiving unit that receives in-vivo information transmitted by the capsule endoscope at a first frequency; an exterior side transmitting unit that transmits the in-vivo information at a second frequency; an exterior side receiving unit that receives a control signal transmitted by the receiving device at the second frequency; and a control unit that controls transmissions and receptions by the interior side receiving unit and the exterior side transmitting unit based on the control signal. The control unit in each of the wireless relay devices transmits a received electrical field intensity that is received from the capsule endoscope via the interior side receiving unit, to the receiving device via the exterior side transmitting unit. The control unit determines, when receiving a selection signal from the receiving device, whether the selection signal is addressed to the wireless relay device itself. The control unit transmits, when determining that the selection signal is addressed to the wireless relay device itself, the in-vivo information received by the interior side receiving unit to the receiving device via the exterior side transmitting unit.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

The best modes for carrying out the present invention will now be explained in detail with reference to the drawings. Embodiments described hereunder are not intended to limit the present invention. In explanations hereunder, each of the drawings is merely a schematic that is depicted in shapes, sizes, and positional relationships for facilitating understanding of the present invention, and therefore, the present invention is not limited to the shapes, the sizes, and the positional relationships exemplarily depicted in each of these drawings.

First Embodiment

Figure 1:
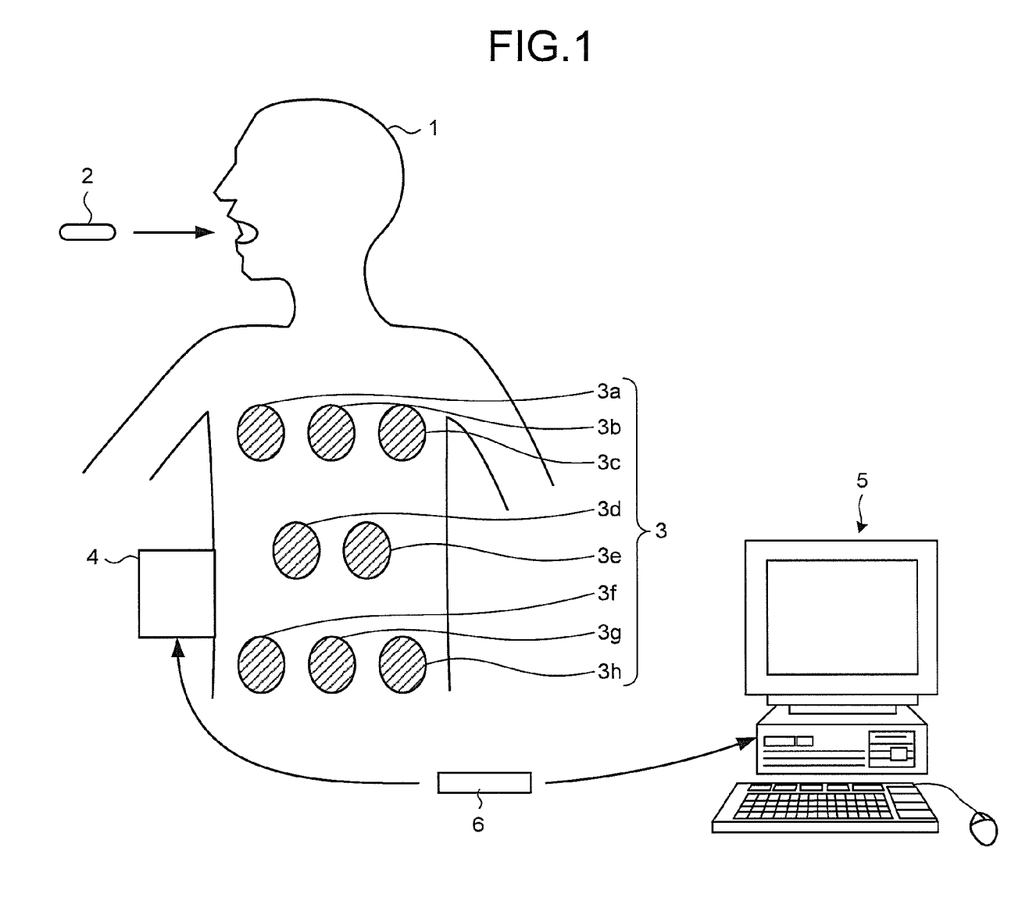
FIG. 1 is a schematic showing a configuration of an in-vivo image acquiring system to which a receiver system according to a first embodiment of the present invention is applied.

FIG. 1 is a schematic showing a configuration of an in-vivo image acquiring system to which a receiver system according to a first embodiment of the present invention is applied. As illustrated in FIG. 1, the in-vivo image acquiring system includes a capsule endoscope 2 that captures in-vivo images of a subject 1, a plurality of wireless relay devices 3 (3a to 3h) that wirelessly relay in-vivo information including the in-vivo images transmitted by the capsule endoscope 2 introduced into the subject 1, a receiving device 4 that receives the in-vivo information wirelessly relayed by each of the wireless relay devices 3 and controls each of the wireless relay devices 3, an image display device 5 that processes and displays thereon the in-vivo images of the subject 1 received by the receiving device 4, and a portable recording medium 6 for transmitting and receiving data between the receiving device 4 and the image display device 5.

The capsule endoscope 2 is introduced into the subject 1, and captures in-vivo images of the subject 1. After being orally swallowed by the subject 1, the capsule endoscope 2 is carried through internal organs by peristaltic motions and the like of the internal organs, while capturing a series of in-vivo images of the subject 1. Every time an in-vivo image of the subject 1 is captured, the capsule endoscope 2 wirelessly transmits an image signal containing the in-vivo image thus captured to the external receiving device 4 via the wireless relay devices 3. Upon doing so, the capsule endoscope 2 transmits each of the in-vivo images of the subject 1 at a time interval corresponding to a unique function of the capsule endoscope 2. For example, the capsule endoscope 2 captures and wirelessly transmits one in-vivo image every two seconds.

Each of the wireless relay devices 3 is disposed on the body surface of the subject 1 in a distributed manner, e.g., along the path where the capsule endoscope 2 introduced into the internal organs of the subject 1 is carried, and is wirelessly connected to the receiving device 4. The wireless relay device 3 captures the image signals that are sequentially wirelessly transmitted from the capsule endoscope 2 being located in the subject 1, and sequentially relays the captured image signals wirelessly to the receiving device 4. The wireless relay devices 3 may also be disposed in a distributed manner on a jacket worn by the subject 1, for example. One or more wireless relay devices 3 need to be disposed, and the number of the devices disposed is not limited to eight.

The receiving device 4 receives the in-vivo images of the subject 1 captured by the capsule endoscope 2 via one of the wireless relay devices 3 with the highest received electrical field intensity, and accumulates therein the received set of in-vivo images. The receiving device 4 includes the portable recording medium 6 attached to the receiving device 4 in a removable manner, and stores the set of in-vivo images of the subject 1 obtained from the capsule endoscope 2 in the portable recording medium 6.

The image display device 5 is realized as a workstation and the like that obtains various types of data such as a set of in-vivo images of the subject 1 via the portable recording medium 6, and displays the various types of data thus obtained onto a display. A physician or a nurse, for example, makes a diagnosis on the subject 1 by observing each of the in-vivo images of the subject 1 displayed on the image display device 5.

The portable recording medium 6 is a portable recording medium, and used for transmitting and receiving data between the receiving device 4 and the image display device 5. Specifically, the portable recording medium 6 has a structure enabled to be attached to and removed from the receiving device 4 and the image display device 5, and to output and to record data when attached to the both.

Figure 2:
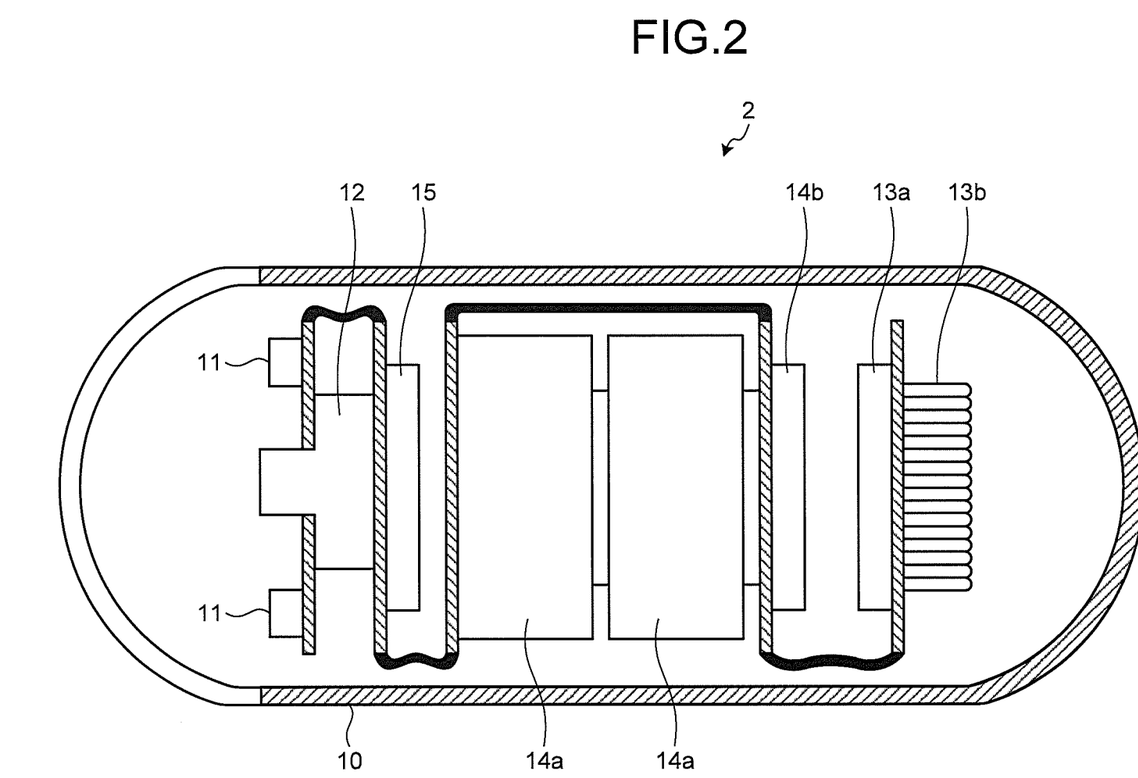
FIG. 2 is a cross-sectional view showing a structure of a capsule endoscope.

FIG. 2 is a cross-sectional view showing a structure of the capsule endoscope 2. As illustrated in FIG. 2, the capsule endoscope 2 includes, inside a capsule-shaped casing 10 formed in a size for allowing easy introduction into the subject 1, a plurality of illuminating units 11 for illuminating the interior of the subject 1, an imaging unit 12 that captures in-vivo images of the interior of the internal organs of the subject 1 illuminated by the illuminating units 11, and a wireless unit 13a and an antenna 13b for wirelessly transmitting the in-vivo images captured by the imaging unit 12 to the exterior. The capsule endoscope 2 also includes a control unit 15 that controls the illuminating units 11, the imaging unit 12, and the wireless unit 13a, and batteries 14a and a power circuit 14b for supplying power to each of these components included in the capsule endoscope 2.

Figure 3:
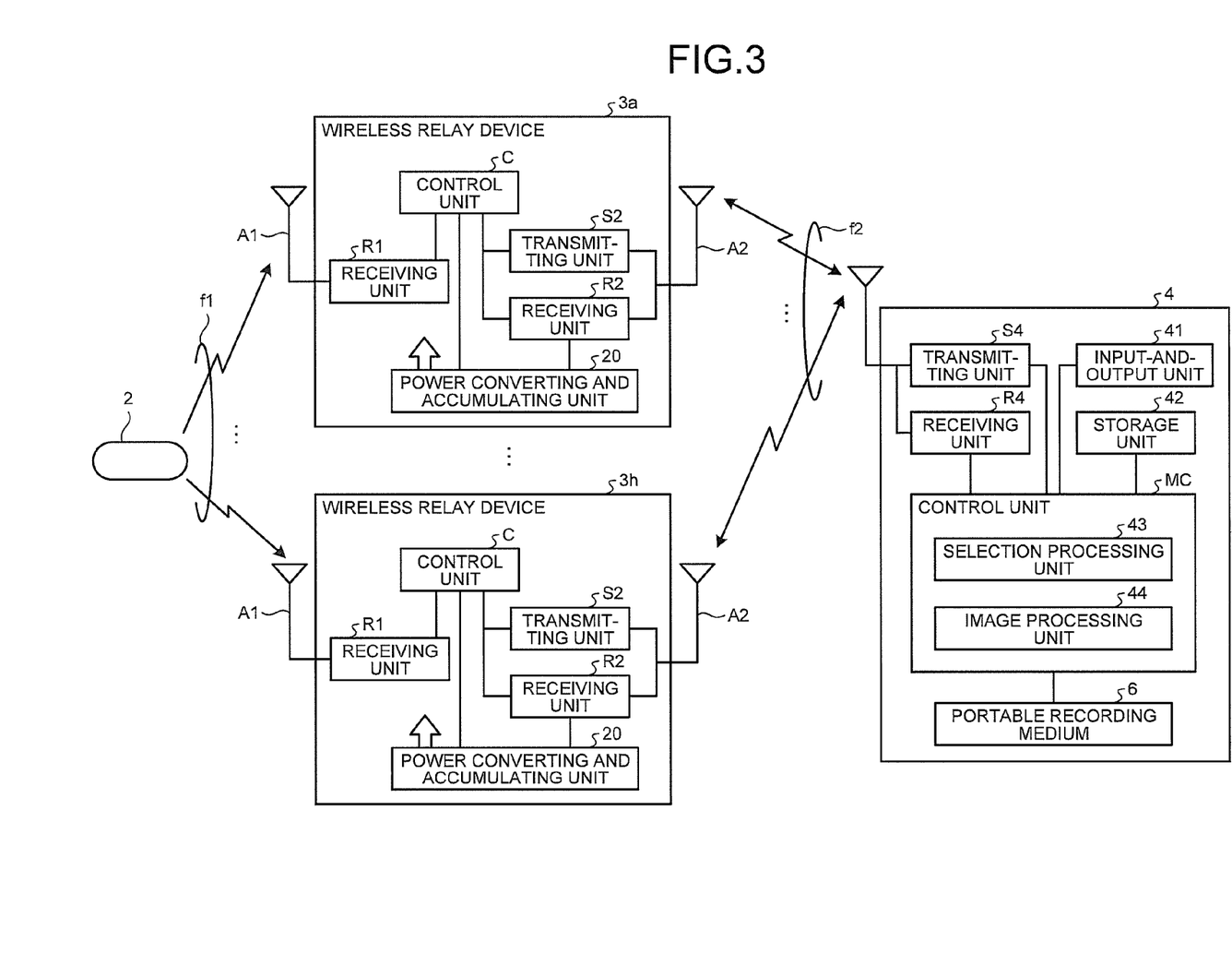
FIG. 3 is a block diagram showing a configuration of the receiver system according to the first embodiment of the present invention.

FIG. 3 is a block diagram showing a configuration of the receiver system according to the first embodiment of the present invention. As illustrated in FIG. 3, this receiver system includes the capsule endoscope 2, the receiving device 4, and the wireless relay devices 3. The wireless relay devices 3 receive in-vivo information including in-vivo images transmitted wirelessly by the capsule endoscope 2 at a frequency f1, and performs wireless transmissions and receptions with the receiving device 4 at a frequency f2 and transmits the in-vivo information received from the capsule endoscope 2 to the receiving device 4 wirelessly. In other words, the wireless frequency f1 between the capsule endoscope 2 and the wireless relay devices 3 and the wireless frequency f2 between the wireless relay devices 3 and the receiving device 4 are made different to prevent crosstalk.

Each of the wireless relay devices 3 includes a receiving antenna A1 and a receiving unit R1 for receiving signals at the frequency f1 transmitted by the capsule endoscope 2 wirelessly. Each of the wireless relay devices 3 also includes an antenna A2, a transmitting unit S2, and a receiving unit R2 for transmitting and receiving signals to and from the receiving device 4 at the frequency f2. Each of the wireless relay devices 3 also includes a control unit C that performs control of the entire wireless relay device, such as transmission and reception control and power control. Each of the wireless relay devices 3 further includes a power converting and accumulating unit 20 that rectifies, power-converts, and accumulates alternating wireless signals received via the antenna A2 and the receiving unit R2. In other words, the wireless relay devices 3 receive wireless waves at the frequency f2 transmitted by the receiving device 4 and convert the power thereof to use the power thus converted as the power source of the wireless relay devices 3. The supply of this accumulated power is controlled under the control of the control unit C.

By contrast, the receiving device 4 includes a transmitting unit S4 that performs transmissions to the wireless relay devices 3 using wireless signals at the frequency f2, a receiving unit R4 that receives wireless signals at the frequency f2 from the wireless relay devices 3, an input-and-output unit 41 that inputs and outputs various types of information, a storage unit 42 that stores therein various computer programs and data, the removable portable recording medium 6, and a control unit MC that controls each of these components. The control unit MC includes a selection processing unit 43 that selects a wireless relay device via which the wireless signals from the capsule endoscope 2 are received at the highest electrical field intensity as a wireless relay device for transferring images, and an image processing unit 44 that applies image processing to received image information.

Figure 4:
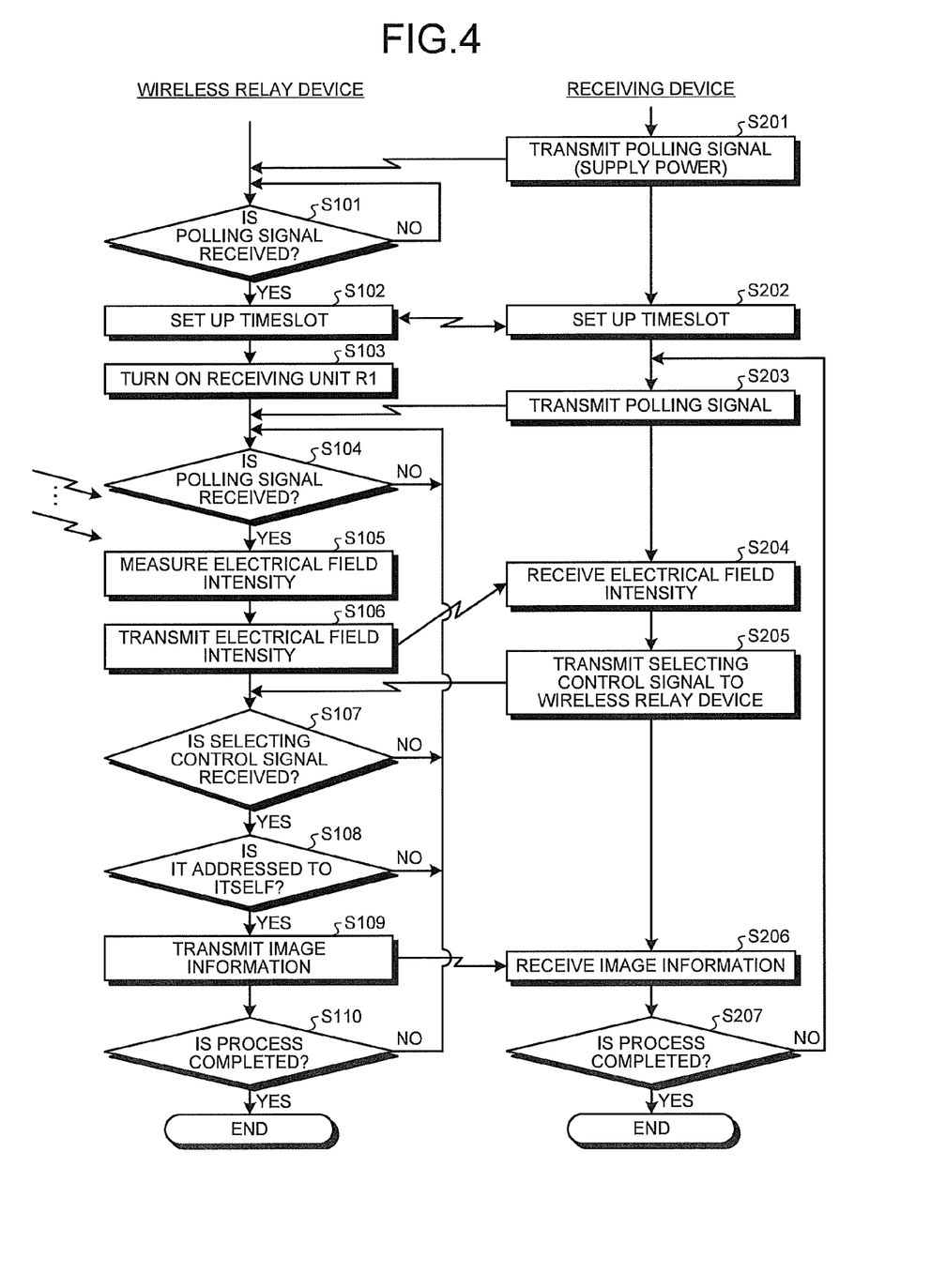
FIG. 4 is a sequence diagram showing transmitting and receiving processes performed between a wireless relay device and a receiving device according to the first embodiment of the present invention.

A wireless relaying process performed by the receiver system will now be explained with reference to the sequence diagram illustrated in FIG. 4. To begin with, the receiving device 4 transmits a polling signal to each of the wireless relay devices 3 (3a to 3h) (Step S201). This polling signal also functions to supply power. Of course, a wireless signal transmitted by the receiving device 4 functions as a signal for supplying power. In response, each of the wireless relay devices 3 determines if the power is supplied upon receiving the polling signal and if the polling signal is received (Step S101), and waits to receive the next polling signal (NO at Step 101). When a polling signal is received (YES at Step S101), the corresponding wireless relay device 3 sets up its own timeslot with the receiving device 4 (Steps S102 and S202). In other words, by allocating a timeslot, the wireless relay device 3 performs an anti-collision process for preventing collisions of communications between the receiving device 4 and each of the wireless relay devices 3. In this anti-collision process, a random number, for example, for deciding the control priority is generated and a timeslot is allocated to each of the wireless relay devices. The wireless relay device 3 then turns ON and starts the receiving unit R1 for receiving the wireless signals from the capsule endoscope 2 (Step S103). The receiving device 4 sends out a polling signal again to each of the wireless relay devices 3 after being allocated with the timeslot (Step S203).

Figure 5:
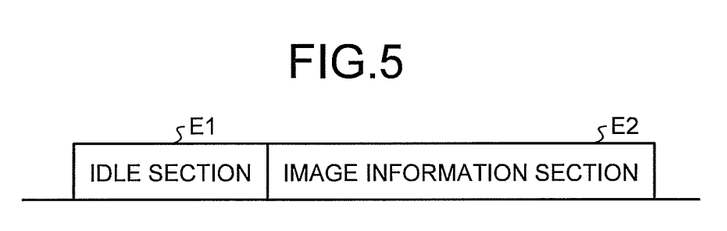
FIG. 5 is a schematic showing a data format of image information.

During this process, the capsule endoscope 2 is transmitting the in-vivo information as a burst signal. The wireless relay device 3 determines if the polling signal from the receiving device 4 is received (Step S104), and waits until the next polling signal is received (NO at Step S104). If the wireless relay device 3 receives the polling signal (YES at Step S104), the wireless relay device 3 measures the electrical field intensity during the period in which the idle section E1, illustrated in the in-vivo information format depicted in FIG. 5, is being transmitted (Step S105). The wireless relay device 3 then transmits the measured received electrical field intensity to the receiving device 4 in the timeslot allocated thereto (Step S106). The idle section E1 includes a synchronization signal for measuring the received electrical field intensity. Of course, a signal for the received electrical field intensity may be included in the idle section E1. An image information section E2 represents the body of information, and contains the image information itself.

Upon receiving the received electrical field intensity (Step S204), the receiving device 4 transmits a selecting control signal for instructing the transmission of the in-vivo information (image information) to the wireless relay device 3 with the highest received electrical field intensity, amongst those from which the received electrical field intensities are received (Step S205).

The wireless relay device 3 determines if the selecting control signal is received (Step S107), and if the selecting control signal is not received (NO at Step S107), goes onto Step S104, further determines if the next polling signal is received, and waits until the next polling signal is received (NO at Step S104). On the contrary, if the selecting control signal is received (YES at Step S107), the wireless relay device 3 further determines if the selecting control signal is addressed to itself (Step S108). If the selecting control signal is not addressed to itself (NO at Step 108), the wireless relay device goes onto Step S104, determines if the next polling signal is received, and waits until the next polling signal is received (NO at Step S104).

On the contrary, if the selecting control signal is addressed to itself (YES at Step S108), the wireless relay device 3 receives the image information, and transmits and relays the information to the receiving device 4 (Step S109). After completing transmitting and relaying the image information, the wireless relay device 3 determines if the process is completed (Step S110). As long as the process is not completed (NO at Step S110), the wireless relay device 3 goes onto Step S104, and waits until the next polling signal is received (NO at Step S104). On the other side, the receiving device 4 receives the transmitted and relayed image information (Step S206). If a completion instruction is then received, the receiving device 4 ends the process (YES at Step S207). As long as no completion instruction is received (NO at Step S207), the receiving device 4 goes onto Step S203, and transmits the next polling signal.

In other words, in this receiver system, because the receiving device 4 and the wireless relay devices 3 are arranged in an one-to-many relationship, the polling signals of the receiving device are used in instructing the wireless relay devices 3 to wirelessly relay the image information. At this time, because the received electrical field intensity needs to be measured with the idle section E1, the reception timing of the image information, which is a burst signal, and the transmission timing of the polling signal need to be synchronized. Because the image information is transmitted at a predetermined interval, e.g., every two seconds, the receiving device 4 controls the timing for transmitting the polling signals by figuring out the predetermined interval to achieve the synchronization. In other words, the reception timing of the polling signals will arrive immediately before receiving the image signal to be received.

Figure 6:
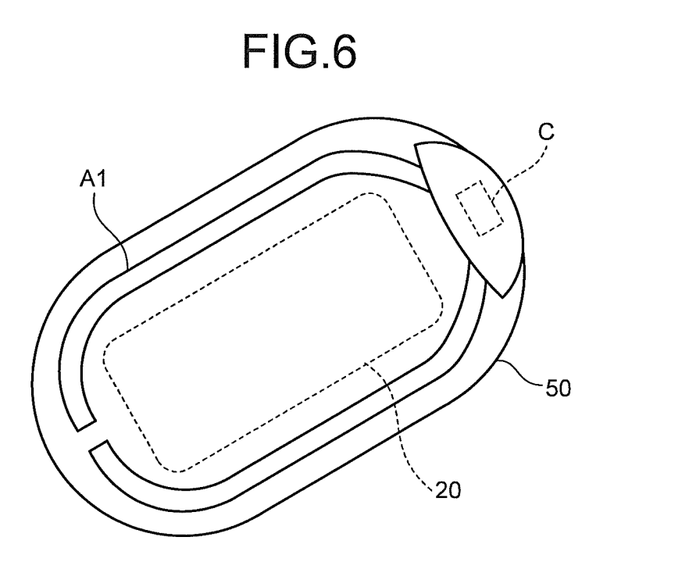
FIG. 6 is a schematic of the wireless relay device according to the first embodiment of the present invention viewed from the rear side.
Figure 7:
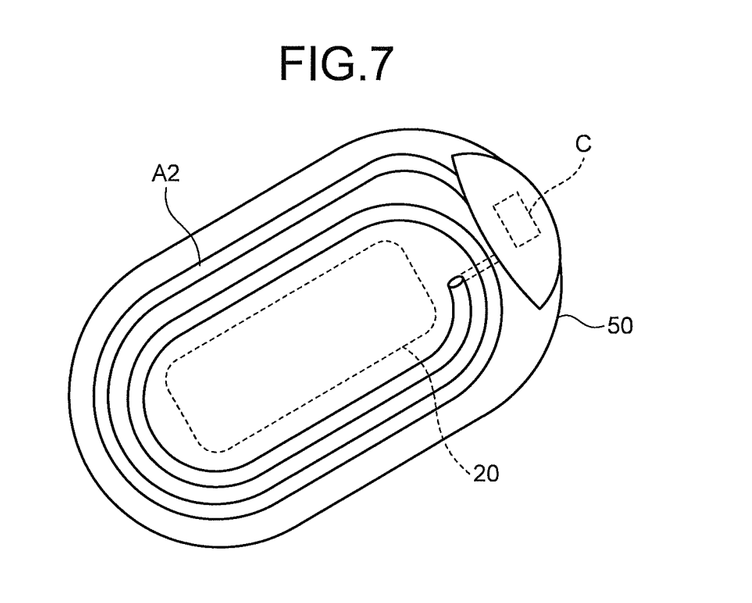
FIG. 7 a schematic of the wireless relay device according to the first embodiment of the present invention viewed from the front side.

In this structure, each of the wireless relay devices 3 is formed in a flat plate like shape, with the antenna A1, the antenna A2, the control unit C, and the power converting and accumulating unit 20 formed integrally to a flexible substrate 50, as illustrated in FIGS. 6 and 7. FIG. 6 shows the wireless relay device viewed from the rear side, that is, from the interior side of the body, and the antenna A1 is formed on the rear side. The antenna A2 is formed on the front side, that is on the exterior side of the body, as illustrated in FIG. 7. Because the antenna A2 needs to receive power supply efficiently, the antenna A2 is formed as a wound spiral coil-like antenna. The antenna A1 on the interior side of the body is exposed because the antenna properties can be improved by bringing the antenna into direct contact with the body surface.

In the first embodiment, because the wireless relay devices 3 are used to wirelessly relay the image information transmitted by the capsule endoscope 2 to the receiving device 4, the antennas (wireless relay devices) can be applied onto the body surface freely without being restricted by the length of the antenna cables, and therefore, can be handled more easily without losing the receiving function of the antennas. Furthermore, because the receiving device 4 is not limited by the presence of the cable and is not necessarily attached to the body surface, a postural change and the like can be made more easily, whereby the freedom for the living body can be improved. Furthermore, unlike the conventional antennas, because the wireless relay devices do not need to be used repeatedly and can be disposed after use, sanitation can be controlled more easily.

Second Embodiment

A second embodiment of the present invention will now be explained. While the wireless relay devices receive power supply by means of wireless waves in the first embodiment, power is supplied using a battery in the second embodiment.

Figure 8:
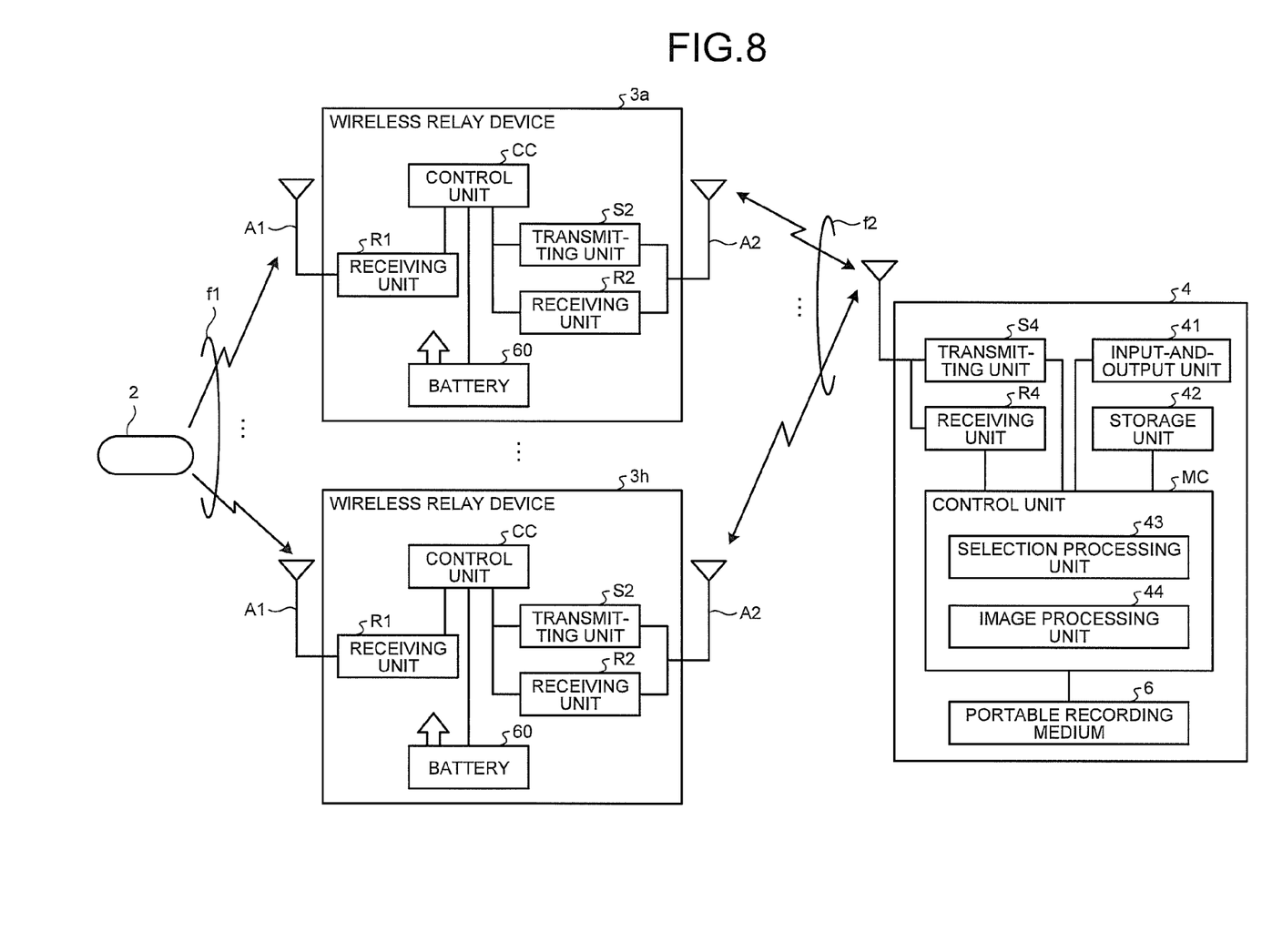
FIG. 8 is a block diagram showing a configuration of a receiver system according to a second embodiment of the present invention.

FIG. 8 is a block diagram showing a configuration of a receiver system according to the second embodiment of the present invention. The receiver system includes a battery 60 such as a button cell instead of the power converting and accumulating unit 20 according to the first embodiment. The receiver system also includes a control unit CC instead of the control unit C. This control unit CC controls to cause the receiving unit R1 to perform receptions intermittently, that is, performs a control process for starting the receiving unit R1 intermittently so as to reduce the battery consumption. Other components are the same as those according to the first embodiment, and the same structural components are given the same reference numerals.

Figure 9:
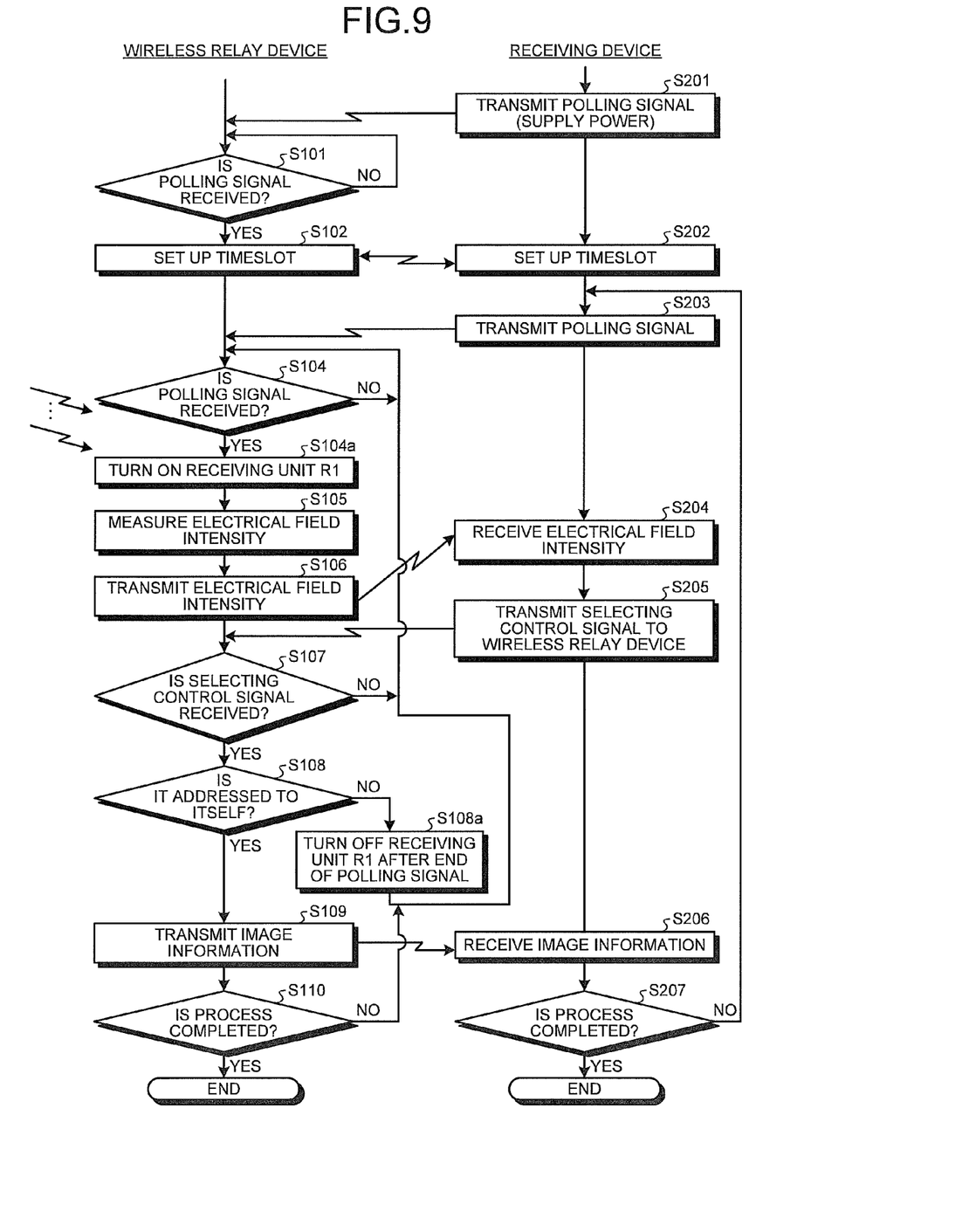
FIG. 9 is a sequence diagram showing transmitting and receiving processes performed between a wireless relay device and a receiving device according to the second embodiment of the present invention.

To realize the intermittent receptions, the sequence illustrated in FIG. 9 is performed. In other words, if the polling signal is received at Step S104, the receiving unit R1 is caused to start (Step S104a), and if the selecting control signal is not addressed to itself at Step S108 (NO at Step S108), the receiving unit R1 is turned OFF after the end of the polling signal (Step S108a). Other steps are the same as those in the sequence illustrated in FIG. 4.

Figure 10:
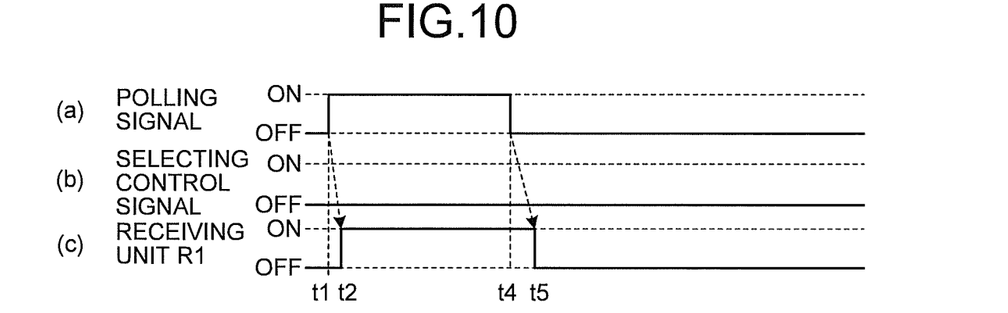
FIG. 10 is a timing chart showing an intermittent starting process performed by a receiving unit being located in a body when the wireless relay device including this receiving unit is not selected.

Next, the intermittent receiving process will be explained with reference to the timing charts illustrated in FIGS. 10 and 11. FIG. 10 illustrates a case in which a particular wireless relay device 3 is not selected by the selecting control signal. As the polling signal (FIG. 10(a)), an ON signal is kept transmitted for the period from the timing t1 to the timing t4. If the selecting control signal is not addressed to the specific device (FIG. 10(b)), the receiving unit R1 rises at the timing t2, which is immediately after the timing t1, as illustrated in FIG. 10(c). The receiving unit R1 is then turned OFF at the timing t5, which is immediately after the timing t4 at which the polling signal ends. In this manner, the power consumed by the receiving unit R1 in the wireless relay devices not relaying the image information wirelessly is reduced.

Figure 11:
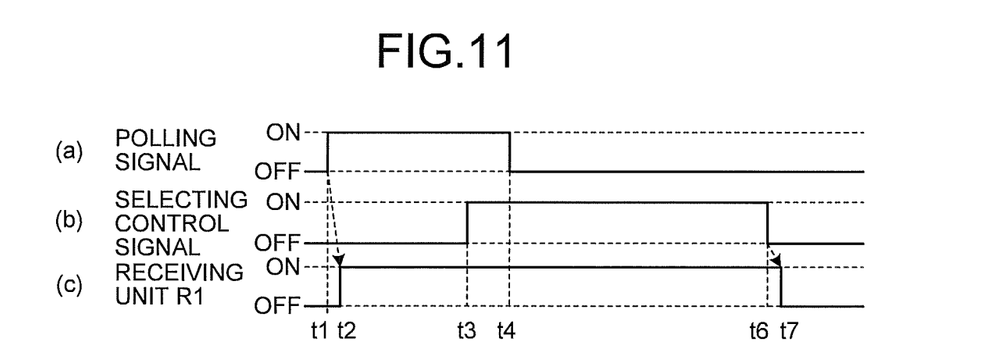
FIG. 11 is a timing chart showing an intermittent starting process performed by the receiving unit being located in the body when the wireless relay device including the receiving unit is selected.

On the contrary, FIG. 11 shows a case where the specific wireless relay device 3 is selected by the selecting control signal. In this case as well, the polling signal illustrated in FIG. 11(a) is the same as the polling signal illustrated in FIG. 10(a). As illustrated in FIG. 11(b), the specific device is selected at the timing t3 by way of transmissions of the received electrical field intensity. The image information is wirelessly transmitted to the receiving device 4 during the period selected by the selecting control signal. Subsequently, when wireless transferring of the image information is completed, the selecting control signal is turned OFF at the timing t6, and the power of the receiving unit R1 is turned OFF immediately thereafter (timing t7), whereby power consumption is reduced.

Figure 12:
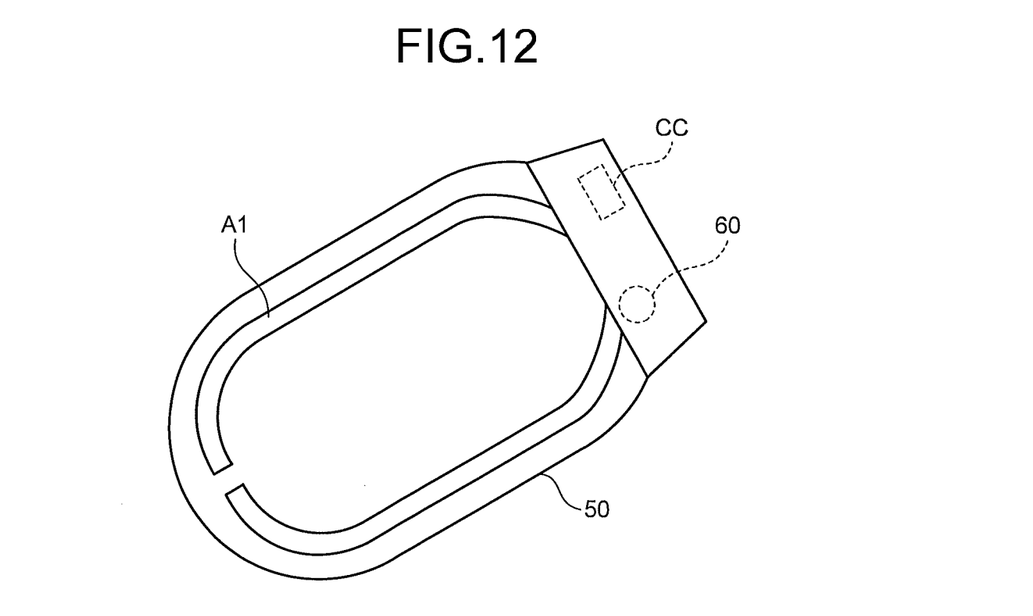
FIG. 12 is a schematic of the wireless relay device according to the second embodiment of the present invention viewed from the rear side.
Figure 13:
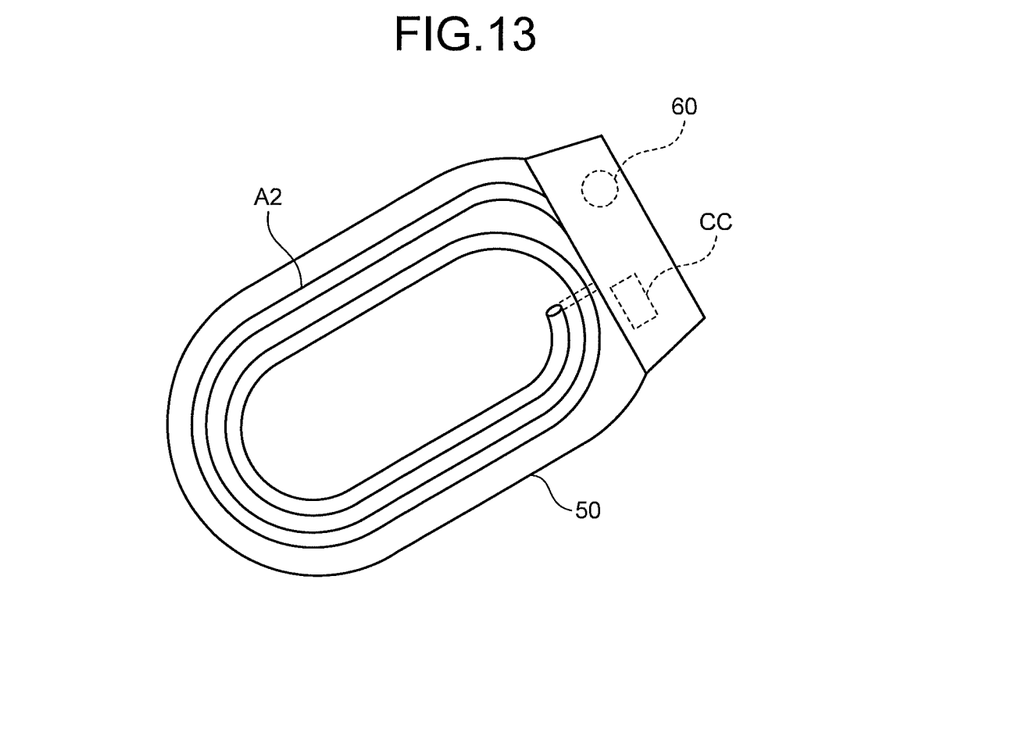
FIG. 13 is a schematic of the wireless relay device according to the second embodiment of the present invention viewed from the front side.

In this structure, each of the wireless relay devices 3 is formed in a flat plate like shape, with the antenna A1, the antenna A2, the control unit CC, and the battery 60 formed integrally to a flexible substrate 50, as illustrated in FIGS. 12 and 13. Other components are the same as those in the structure illustrated in FIGS. 6 and 7. However, because the antenna A2 does not need to receive the power, the antenna A2 is not necessarily a long coil-like antenna. Rather, a small antenna can be realized. In other words, when the efficiency of the power reception is considered, the wireless frequency f1 needs to be low. However, without considering the efficiency of the power reception, an antenna for a high wireless frequency may be used. As a consequence, a small antenna can be used. In addition, the shape of the antenna can be designed freely.

In the second embodiment, because the wireless relay devices 3 are used to wirelessly relay the image information transmitted by the capsule endoscope 2 to the receiving device 4 in the same manner as in the first embodiment, the antennas (wireless relay devices) can be applied onto a body surface freely without being restricted by the length of the antenna cable, and therefore, can be handled more easily without losing the receiving function of the antennas. Furthermore, because the receiving device 4 is not limited by the presence of the cable and is not necessarily attached to the body surface, a postural change and the like can be made more easily, whereby the freedom for the living body can be improved. Furthermore, unlike the conventional antennas, because the wireless relay devices do not need to be used repeatedly and can be disposed after use, sanitation can be controlled more easily. Furthermore, while a battery is used as the source of the power supply, because the receiving unit R1 is started intermittently, power consumption can be reduced, and a system being feasible for practical applications can be realized.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A receiving system comprising:
    an ex-vivo device for processing in-vivo information acquired by a capsule endoscope configured to be introduced into a subject; and
    a plurality of relay devices for relaying the in-vivo information acquired by the capsule endoscope to the ex-vivo device, the plurality of relay devices comprising:
        a first relay device comprising a first receiving unit and a first transmitting unit; and
        a second relay device comprising a second receiving unit and a second transmitting unit;
    wherein the first receiving unit and the second receiving unit are each configured to wirelessly receive an in-vivo information signal transmitted from the capsule endoscope, wherein the in-vivo information signal carries the in-vivo information,
    wherein the first receiving unit is configured to measure a first electrical field intensity of the in-vivo information signal received by the first receiving unit, and the second receiving unit is configured to measure a second electrical field intensity of the in-vivo information signal received by the second receiving unit, wherein the ex-vivo device is configured to transmit a polling signal to each of the first relay device and the second relay device, wherein the first transmitting unit is configured to transmit a first electrical field intensity signal carrying the first electrical field intensity in response to the polling signal, and the second transmitting unit is configured to transmit a second electrical field intensity signal carrying the second electrical field intensity in response to the polling signal, wherein the ex-vivo device is configured
- to compare the first electrical field intensity signal and the second electrical field intensity signal to determine that the first electrical field intensity is stronger than the second electrical field intensity, and
- to transmit a selection signal identifying the first relay device as a selected relay device based on the determination that the first electrical field intensity is stronger, and wherein the first transmitting unit is configured to transmit an in-vivo information relay signal carrying the in-vivo information to the ex-vivo device, in response to the selection signal transmitted by the ex-vivo device.

2. The receiving system according to claim 1, wherein each of the ex-vivo device and the plurality of relay devices have an anti-collision function.

3. The receiving system according to claim 1, wherein each of the plurality of relay devices further comprise a power converting and accumulating unit configured to convert at least one of the polling signal and the selection signal transmitted by the ex-vivo device to power and to accumulate therein the power.

4. The receiving system according to claim 1, wherein each of the plurality of relay devices further comprise a battery configured to supply power to the first receiving unit, the first transmitting unit, the second receiving unit and the second transmitting unit, respectively.

5. The receiving system according to claim 1, wherein each of the plurality of relay devices further comprise a control unit configured to perform intermittent reception control,
    wherein the control unit of the first relay device is configured to control the first receiving unit to start wirelessly receiving the in-vivo information signal in response to the polling signal;
    wherein the control unit of the second relay device is configured to:
        control the second receiving unit to start wirelessly receiving the in-vivo information signal in response to the polling signal;
        determine that the selecting signal has not been received after a predetermined time period;
        determine that the selecting signal does not identify the second relay device as the selected relay device; and
        control the second receiving unit to stop wirelessly receiving the in-vivo information signal when the control unit determines that the selecting signal has not been received after a predetermined time period or determines that the selecting signal does not identify the second relay device as the selected relay device.

6. The receiving system according to claim 1,
wherein each of the first relay device and the second relay device further comprises:
    a plate-like dielectric member;
    a subject-side antenna arranged to one surface of the plate-like dielectric member, the subject-side antenna being configured to wirelessly receive the in-vivo information signal transmitted from the capsule endoscope introduced into the subject; and
    an ex-vivo-side antenna arranged to another surface of the plate-like dielectric member, the ex-vivo-side antenna being configured to wirelessly receive and wirelessly transmit the polling signal, the selection signal, the first electrical field intensity signal, the second electrical field intensity signal, and the in-vivo information relay signal, respectively,
    wherein the first relay device and the second relay device are configured such that the one surface of the plate-like dielectric member is arranged to face a surface of the subject.

7. The receiving system according to claim 6,
wherein the first receiving unit and the first transmitting unit is arranged on the plate-like dielectric member or in the plate-like dielectric member of the first relay device, and
wherein the second receiving unit and the second transmitting unit is arranged on the plate-like dielectric member or in the plate-like dielectric member of the second relay device.

8. A receiving system comprising:
a plurality of relay devices for relaying an in-vivo information acquired by a capsule endoscope configured to be introduced into a subject, to an ex-vivo device, the plurality of relay devices comprising:
    a first relay device comprising a first receiving unit and a first transmitting unit; and
    a second relay device comprising a second receiving unit and a second transmitting unit;
wherein the first receiving unit and the second receiving unit are each configured to wirelessly receive an in-vivo information signal transmitted from the capsule endoscope, wherein the in-vivo information signal carries the in-vivo information,
wherein the first receiving unit is configured to measure a first electrical field intensity of the in-vivo information signal received by the first receiving unit, and the second receiving unit is configured to measure a second electrical field intensity of the in-vivo information signal received by the second receiving unit,
wherein the first transmitting unit is configured to transmit a first electrical field intensity signal carrying the first electrical field intensity in response to a polling signal transmitted from the ex-vivo device, and the second transmitting unit is configured to transmit a second electrical field intensity signal carrying the second electrical field intensity in response to the polling signal transmitted from the ex-vivo device, and
wherein the first transmitting unit is configured to transmit an in-vivo information relay signal carrying the in-vivo information to the ex-vivo device, in response to a selection signal transmitted by the ex-vivo device, the selection signal identifying the first relay device as a selected relay device based on comparison of the first electrical field intensity signal and the second electrical field intensity signal by the ex-vivo device to determine that the first electrical field intensity is stronger than the second electrical field intensity.

9. The receiving system according to claim 8, wherein each of the ex-vivo device and the plurality of relay devices have an anti-collision function.

10. The receiving system according to claim 8, wherein each of the plurality of relay devices further comprise a power converting and accumulating unit configured to convert at least one of the polling signal and the selection signal transmitted by the ex-vivo device to power and to accumulate therein the power.

11. The receiving system according to claim 8, wherein each of the plurality of relay devices further comprise a battery configured to supply power to the first receiving unit, the first transmitting unit, the second receiving unit and the second transmitting unit, respectively.

12. The receiving system according to claim 8, wherein each of the plurality of relay devices further comprise a control unit configured to perform intermittent reception control,
wherein the control unit of the first relay device is configured to control the first receiving unit to start wirelessly receiving the in-vivo information signal in response to the polling signal;
wherein the control unit of the second relay device is configured to:
control the second receiving unit to start wirelessly receiving the in-vivo information signal in response to the polling signal;
determine that the selecting signal has not been received after a predetermined time period;
determine that the selecting signal does not identify the second relay device as the selected relay device; and
control the second receiving unit to stop wirelessly receiving the in-vivo information signal when the control unit determines that the selecting signal has not been received after a predetermined time period or determines that the selecting signal does not identify the second relay device as the selected relay device.

13. The receiving system according to claim 8,
wherein each of the first relay device and the second relay device further comprises:
a plate-like dielectric member;
a subject-side antenna arranged to one surface of the plate-like dielectric member, the subject-side antenna being configured to wirelessly receive the in-vivo information signal transmitted from the capsule endoscope introduced into the subject; and
an ex-vivo-side antenna arranged to another surface of the plate-like dielectric member, the ex-vivo-side antenna being configured to wirelessly receive and wirelessly transmit the polling signal, the selection signal, the first electrical field intensity signal, the second electrical field intensity signal, and the in-vivo information relay signal, respectively,
wherein the first relay device and the second relay device are configured such that the one surface of the plate-like dielectric member is arranged to face a surface of the subject.

14. The receiving system according to claim 13,
wherein the first receiving unit and the first transmitting unit is arranged on the plate-like dielectric member or in the plate-like dielectric member of the first relay device, and
wherein the second receiving unit and the second transmitting unit is arranged on the plate-like dielectric member or in the plate-like dielectric member of the second relay device.

* * * * *